(12) United States Patent
Okamoto

(10) Patent No.: US 6,894,196 B2
(45) Date of Patent: May 17, 2005

(54) PROCESS FOR PRODUCING A FLUORINATED ALCOHOL

(75) Inventor: Hidekazu Okamoto, Yokohama (JP)

(73) Assignee: Asahi Glass Company, Limited, Tokyo (JP)

( * ) Notice: Subject to any disclaimer, the term of this patent is extended or adjusted under 35 U.S.C. 154(b) by 46 days.

(21) Appl. No.: 10/370,507

(22) Filed: Feb. 24, 2003

(65) Prior Publication Data

US 2003/0149312 A1 Aug. 7, 2003

Related U.S. Application Data

(63) Continuation of application No. PCT/JP01/07257, filed on Aug. 24, 2001.

(30) Foreign Application Priority Data

Aug. 24, 2000 (JP) .................................... 2000-254433

(51) Int. Cl.[7] .................... C07C 31/34; C07C 31/38; C07C 31/40; C07C 31/42
(52) U.S. Cl. .................. 568/842; 568/840; 568/841; 568/843
(58) Field of Search ................ 570/842, 840, 570/841, 843; 568/842, 840, 841, 843

(56) References Cited

U.S. PATENT DOCUMENTS 4,346,250 A    8/1982   Satokawa et al.

FOREIGN PATENT DOCUMENTS

| EP | 0 811 594 A1 | 12/1997 |
| EP | 0 968 990 A2 | 1/2000 |
| WO | WO 01/14298 A1 | 3/2001 |

OTHER PUBLICATIONS

U.S. Appl. No. 10/077,794, filed Feb. 20, 2002, Wada et al.
U.S. Appl. No. 10/131,187, filed Apr. 25, 2002, Okamoto.
U.S. Appl. No. 10/298,652, filed Nov. 19, 2002, Okamoto et al.
U.S. Appl. No. 10/028,827, filed Dec. 28, 2001, Wada et al.
U.S. Appl. No. 10/370,507, filed Feb. 24, 2003, Okamoto.

*Primary Examiner*—Elvis O. Price
(74) *Attorney, Agent, or Firm*—Oblon, Spivak, McClelland, Maier & Neustadt, P.C.

(57) ABSTRACT

A process for producing a high-purity fluorinated alcohol in a good purification yield, is provided.

In a process for producing a fluorinated alcohol, which comprises reacting methanol with tetrafluoroethylene or hexafluoropropylene in the presence of an alkyl peroxide, the reaction liquid after completion of the reaction is distilled in the presence of water and HF to separate it into a fraction containing an alcohol derived from the alkyl peroxide and a bottom liquid containing the fluorinated alcohol, and then, the bottom liquid is purified to recover the fluorinated alcohol.

18 Claims, 2 Drawing Sheets

PROCESS FOR PRODUCING A FLUORINATED ALCOHOL

TECHNICAL FIELD

The present invention relates to a process for producing a fluorinated alcohol. The fluorinated alcohol in the present invention, is useful as a solvent in a process for preparing e.g. a photoreceptor for a film or a recording layer for an information recording medium (such as an optical disk such as CD-R or DVD-R) having a recording layer capable of writing and/or reading information by a laser formed on a substrate.

BACKGROUND ART

As a method for producing a fluorinated alcohol of the formula $H(CF_2CF_2)_mCH_2OH$ (wherein m is 1 or 2), (1) a method is known in which excess methanol and tetrafluoroethylene are reacted in the presence of a dialkyl peroxide such as tert-butyl octyl peroxide as a reaction initiator to produce it as a telomer mixture of $H(CF_2CF_2)_kCH_2OH$ (wherein k is an integer of from 1 to 12) (JP-A-54-154707 and U.S. Pat. No. 2,559,628).

Further, (2) as a method for purifying the telomer mixture, a method has been proposed in which methanol is distilled from the top of a distillation column, and as a side cut fraction, water and HF are distilled, and as a bottom liquid, a fluorinated alcohol is obtained (Japanese Patent No. 3,026,804).

In the telomer mixture of the method (1), an alcohol which is a decomposition product of the dialkyl peroxide, is usually contained, and there has been a problem that in the presence of such an alcohol, the purification yield of the fluorinated alcohol tends to be low. Further, in the method (2), together with the fluorinated alcohol, an alcohol as a decomposition product will remain in the bottom liquid, and there has been a problem that in the subsequent step, the load of the distillation step to obtain a high purity fluorinated alcohol, tends to be heavy, and the yield of the fluorinated alcohol also tends to be low.

It is an object of the present invention to solve the above problems and to provide a process for producing a fluorinated alcohol, whereby the desired fluorinated alcohol can be produced in good yield, and highly efficient purification can be carried out in a small number of process steps.

DISCLOSURE OF THE INVENTION

The present inventors have found that the alcohol formed from the alkyl peroxide used as a radical initiator will have a certain interaction with the desired fluorinated alcohol, whereby the efficiency in the purification step by distillation is deteriorated.

Further, the present inventors have conducted an extensive study on the process for separating and purifying the reaction liquid after the reaction containing such an alcohol and as a result, have arrived at the present invention whereby the desired fluorinated alcohol can be obtained in high yield by carrying out distillation in the coexistence of HF and water present in the reaction liquid to distill the alcohol as concentrated on a low boiling fraction containing HF and water.

Namely, the present invention provides a process for producing a fluorinated alcohol, which comprises reacting methanol with tetrafluoroethylene or hexafluoropropylene in the presence of an alkyl peroxide to produce a fluorinated alcohol of the following formula (1):

$H(CFR^1CF_2)_nCH_2OH$ (1)

wherein n is 1 or 2, and when n is 1, $R^1$ is F or $CF_3$, and when n is 2, $R^1$ is F, wherein the reaction liquid after completion of the reaction is distilled in the presence of water and HF to separate it into a fraction containing an alcohol derived from the alkyl peroxide and a bottom liquid containing the fluorinated alcohol of the formula (1), and then, the bottom liquid is purified to recover the fluorinated alcohol of the formula (1).

BEST MODE FOR CARRYING OUT THE INVENTION

Figure 1:
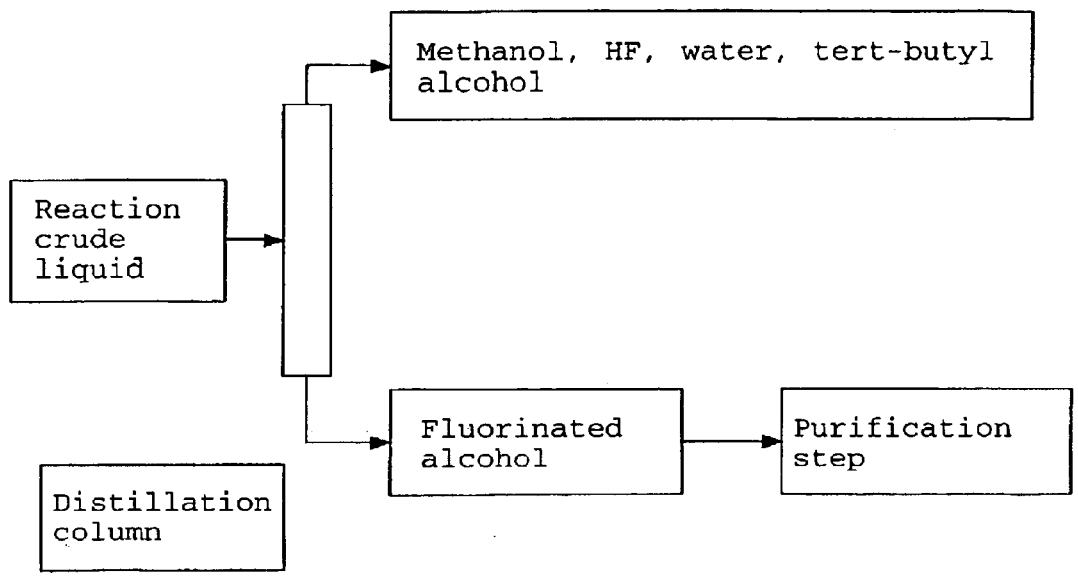
FIG. 1 is an embodiment for carrying out the process for producing a fluorinated alcohol of the present invention and is a flow chart of a case wherein a reaction crude liquid is separated by distillation into a fraction which contains an alcohol derived from an alkyl peroxide and a bottom liquid at the bottom of the distillation apparatus, which contains the fluorinated alcohol.

Now, practical embodiments of the present invention will be described in detail.

In the process of the present invention, methanol is reacted with tetrafluoroethylene or hexafluoropropylene in the presence of an alkyl peroxide. Here, it is preferred to use methanol in an excess amount relative to tetrafluoroethylene or hexafluoropropylene. Use of methanol in an excess amount is advantageous in that it improves the yield of a fluorinated alcohol of the formula (1) wherein n is 1 or 2 (hereinafter referred to as the fluorinated alcohol).

It is preferred to use the alkyl peroxide in an amount of from 0.1 to 5 mass % based on the amount of methanol.

The reaction temperature for the above reaction is preferably from about 80 to 150° C., particularly preferably from 100 to 140° C. Further, the reaction pressure is preferably from about 0.5 to 1.2 MPa (gauge pressure, the same applies hereinafter). The reaction can be carried out in a reactor such as an autoclave. The reactor is preferably flushed with an inert gas such as nitrogen gas or argon gas.

The reaction of methanol with tetrafluoroethylene or hexafluoropropylene may be carried out in the presence of an acid acceptor, but may be carried out in the absence thereof without any trouble. The acid acceptor may, for example, be an inorganic compound, such as an oxide, hydroxide or carbonate, or an alkali metal (such as sodium or potassium), an alkaline earth metal (such as magnesium, calcium or barium) or zinc, ammonium hydroxide or ammonium carbonate, or an organic compound such as an alkali metal alcoholate.

The alkyl peroxide used in the above reaction, acts as a radical initiator. As such an alkyl peroxide, a compound of the following formula (2) is preferred.

$R^3$—O—O—$R^2$ (2)

wherein $R^3$ is a $C_{1-20}$ aliphatic hydrocarbon group, and $R^2$ is a $C_{1-20}$ aliphatic hydrocarbon group or an aromatic hydrocarbon group.

The $C_{1-20}$ aliphatic hydrocarbon group is preferably an aliphatic saturated hydrocarbon group, which may, for example, be an alkyl group, a cycloalkyl group or a cycloalkylalkyl group, and particularly preferred is an alkyl group. Further, the aromatic hydrocarbon group may, for example, be a phenyl group or a phenyl group having a substituent.

As the compound of the formula (2), a compound of the following formula (2a) is particularly preferred:

$C(CH_3)_3$—O—O—$R^2$ (2a)

wherein $R^2$ is a $C_{1-20}$ aliphatic hydrocarbon group or an aromatic hydrocarbon group.

Further, $R^2$ is preferably a $C_{1-20}$ aliphatic saturated hydrocarbon group, particularly preferably a $C(CH_3)_3$— group (a tert-butyl group).

Namely, the compound of the above formula (2a) has a half life of from about 8 to 10 hours in the optimum reaction temperature range of from 100 to 140° C., and accordingly, when the reaction is carried out at a temperature of at least 100° C., formation of telomers of the formula (1) wherein n is at least 3, can be prevented, and the desired fluorinated alcohol wherein n is 1 or 2, can selectively be prepared, and further at that temperature, the compound of the formula (2a) will effectively acts and is decomposed.

Specific examples of the alkyl peroxide of the formula (2) include di-tert-butyl peroxide (Perbutyl D, tradename, manufactured by NOF Corporation), tert-butyl peroxy-2-ethyl hexanoate (Perbutyl O, tradename, manufactured by NOF Corporation), tert-butyl peroxy isopropyl carbonate (Perbutyl I, tradename, manufactured by NOF Corporation) and tert-butyl cumyl peroxide (Perbutyl C, tradename, manufactured by NOF Corporation). Among them, Perbutyl D is most preferred from the viewpoint of the half life of 10 hours and general applicability.

Further, as a radical initiator other than the above, UV, heat, an azo type initiator or a photoradical initiator may, for example, be mentioned. Such a radical initiator may be used in combination with the alkyl peroxide.

In the present invention, the alcohol derived from the alkyl peroxide may be $R^3$—OH (wherein $R^3$ is as defined in the formula (2)), in a case where the alkyl peroxide in a compound of the formula (2). Further, in a case where $R^2$ is a $C_{1-20}$ aliphatic hydrocarbon group, $R^2$—OH will also be formed as an alcohol derived from the alkyl peroxide. As a specific example of the alcohol derived from the alkyl peroxide, tert-butyl alcohol or 2-ethyl hexyl alcohol may be mentioned.

In a case where $R^2$ in the compound of the formula (2) or in the compound of the formula (2a), is an aromatic hydrocarbon group, $R^2$—OH formed by the decomposition of the alkyl peroxide will likely be a higher boiling component than $R^3$—OH or tert-butyl alcohol and will likely be contained in the bottom liquid, although such may depend also on the structure of $R^2$. In such a case, in the purification of the bottom liquid as described hereinafter, such $R^2$—OH and the fluorinated alcohol can easily be separated.

The process of the present invention is characterized in that the fluorinated alcohol and the alcohol derived from an alkyl peroxide, which can, if coexistent, hardly be separated by distillation, are initially separated under certain specific distillation conditions, and then the fluorinated alcohol contained in the bottom liquid, is purified by a further purification step. It is thereby possible to obtain a high purity fluorinated alcohol in small number of steps.

Figure 2:
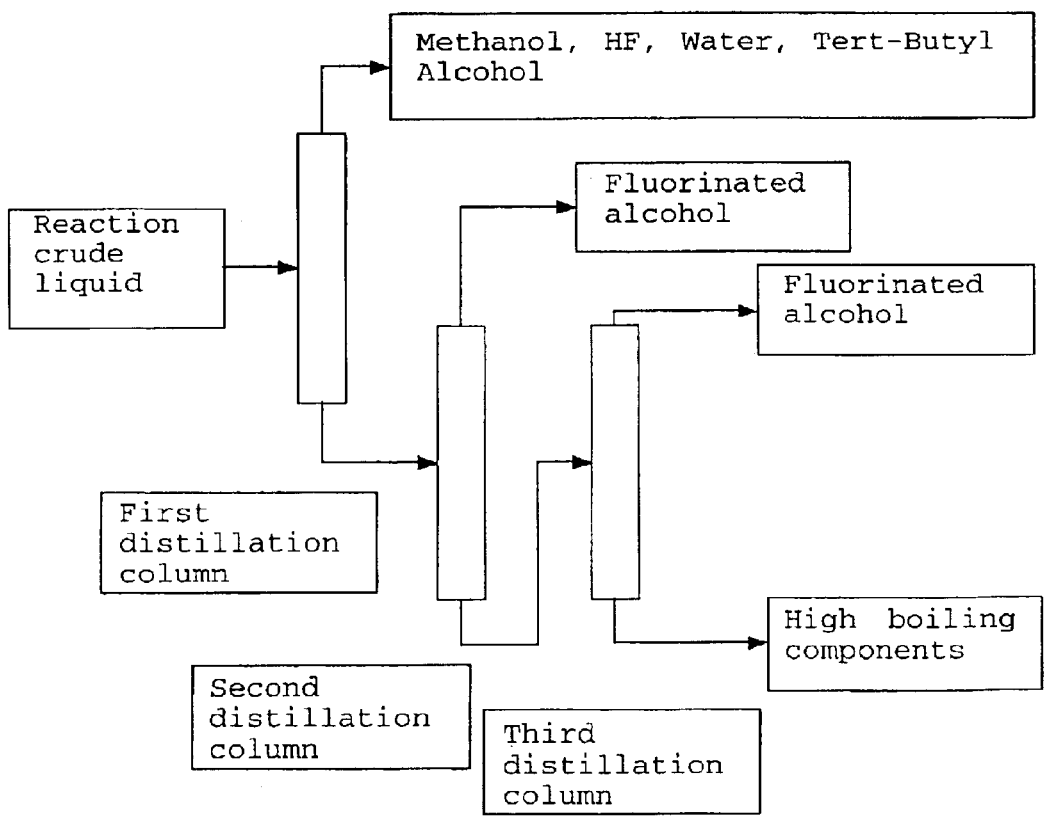
FIG. 2 is a flow chart of one embodiment of the present invention in which the purification step of the bottom liquid which contains the fluorinated alcohol, in FIG. 1, is distillation.
Figure 3:
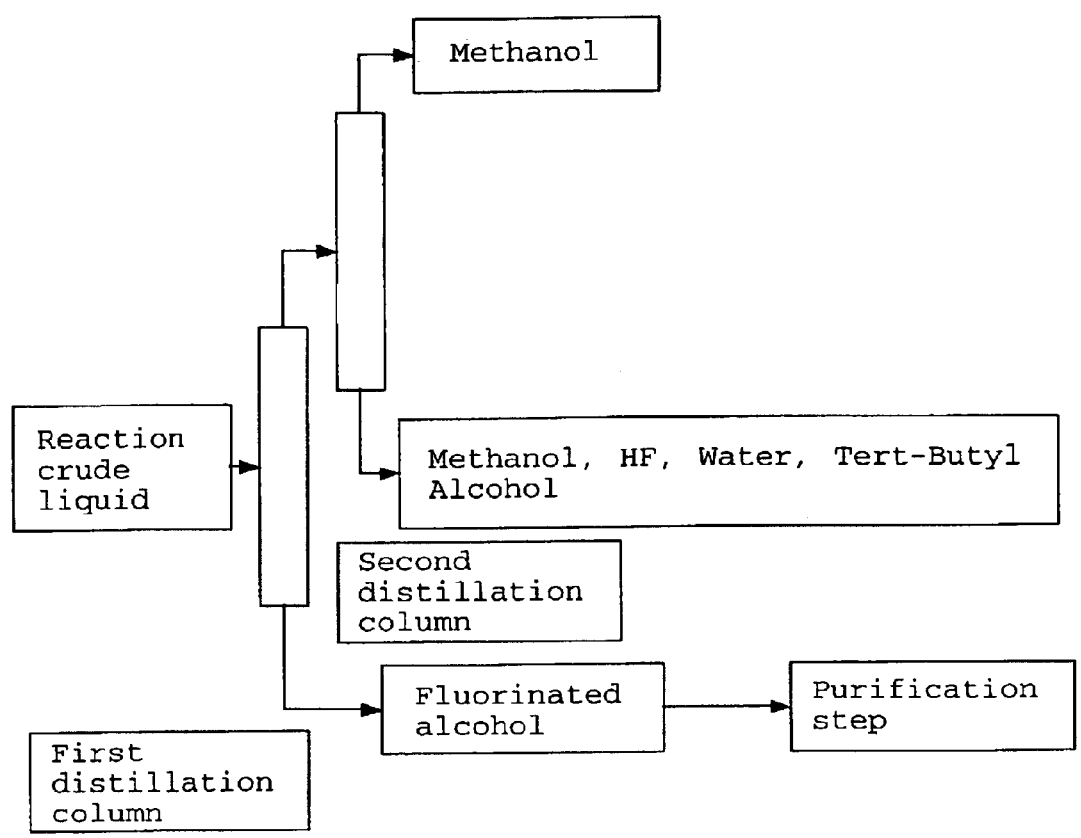
FIG. 3 is a flow chart of one embodiment of the present invention which includes a step of further distilling the first fraction to recover methanol from the first fraction in FIG. 1.

FIGS. 1 to 3 are flow charts illustrating embodiments of the present invention, respectively. Now, a case wherein $C(CH_3)_3$—O—O—$C(CH_3)_3$ is used as the alkyl peroxide, will be described.

The reaction liquid after completion of the reaction having methanol reacted with tetrafluoroethylene or hexafluoropropylene, will be led to a distillation step from the reactor.

The reaction liquid (hereinafter referred to as the reaction crude liquid) after completion of the reaction prior to the distillation step, contains the desired fluorinated alcohol, unreacted methanol, an alcohol derived from the alkyl peroxide, which is, here, $C(CH_3)_3$—OH (hereinafter referred to as tert-butyl alcohol) formed as derived from $C(CH_3)_3$—O—O—$C(CH_3)_3$, and an undecomposed alkyl peroxide.

The reaction crude liquid may be distilled directly as it is, but in a case where a solid content or the like is present, filtration or the like may be carried out as the case requires. In the process of the present invention, it is not necessary to give the heat treatment the reaction crude liquid, and it is preferred to distil it substantially directly.

The amount of the alcohol derived from the alkyl peroxide contained in the reaction crude liquid, is usually from about 1,000 to 10,000 ppm.

In order to have tert-butyl alcohol efficiently concentrated on the fraction side from the reaction crude liquid in the distillation step, it is preferred that HF and water are coexistent in sufficient amounts in the reaction crude liquid before the distillation. For this purpose, it is preferred to add water or HF as the case requires to adjust the amounts of water and HF in the reaction crude liquid. The content of water in the reaction crude liquid after the addition, is preferably from 0.1 to 10 mass %, more preferably from 0.5 to 10 mass %, particularly preferably from 1 to 10 mass %. Further, the content of HF in the reaction crude liquid after the addition, is preferably from 0.01 to 10 mass %, more preferably from 0.01 to 5 mass %.

FIG. 1 shows a flow chart of a case wherein the reaction crude liquid is separated by distillation into a fraction which contains an alcohol derived from the alkyl peroxide and a bottom liquid at the bottom of the distillation apparatus containing the fluorinated alcohol (the bottom liquid will be sent to the purification step).

In the distillation step, it is preferred to carry out the distillation by means of a distillation column from the viewpoint of the precision in distillation. As the distillation column, it is preferred to employ one having a theoretical plate number of from 10 to 100 plates.

In the distillation step, the reaction crude liquid is distilled in the presence of water and HF. And, the reaction crude liquid is separated into a fraction containing an alcohol (here, tert-butyl alcohol) derived from the alkyl peroxide and a bottom liquid at the bottom of distillation apparatus containing the fluorinated alcohol. For this purpose, it is preferred that the above reaction crude liquid is heated under such conditions that the gauge pressure is from 0 to 0.1 MPa, preferably 0 MPa (i.e. the atmospheric pressure) and the distillation temperature is from 40 to 130° C., preferably from 60 to 130° C.

Tert-butyl alcohol is preferably separated from the reaction crude liquid as a fraction containing methanol, HF and water. Further preferably, the fraction containing tert-butyl alcohol is distilled from the top of the distillation column, and it is particularly preferred that the fraction mainly containing methanol, HF and water together with tert-butyl alcohol, is distilled from the top of the column.

The content of tert-butyl alcohol in the bottom liquid after distillation (hereinafter referred to as the initial distillation) of the reaction crude liquid, in other words, the tert-butyl alcohol-remaining ratio, is preferably as low as possible. In a case where a usual distillation apparatus is employed, the tert-butyl alcohol remaining ratio is preferably adjusted to be at most 1,000 ppm (not including 0) to the bottom liquid. The adjustment to a level of at most 1,000 ppm (not including 0) is advantageous in that the purity of the fluorinated alcohol can easily be increased, when the subsequent purification step is carried out depending upon the desired purity. For example, if it is at most 1,000 ppm (not including 0), in the purification step which will be described next, a fluorinated alcohol having a purity of at least 99.9 mass %, can be recovered at least 50%, based on the content of fluorinated alcohol in the reaction crude liquid.

FIG. 2 is a flow chart of a case wherein the purification step of the bottom liquid containing the fluorinated alcohol in FIG. 1, is distillation. The bottom liquid recovered from the distillation apparatus (the first distillation column in FIG. 2) in the distillation step, will be led to a purification step. The method for the purification step is not limited, but is preferably distillation (the second distillation column in FIG. 2). By distilling the bottom liquid by the second distillation column (hereinafter referred to as the second distillation), the fluorinated alcohol as the desired component can be recovered as of a high purity. Further, in a case where the fluorinated alcohol is recovered in the second distillation, it is preferred to recover the fluorinated alcohol as a fraction as shown in FIG. 2 rather than recovering it as a bottom liquid, since the fluorinated alcohol of higher purity can thereby be recovered. Further, the purification step for the bottom liquid containing the fluorinated alcohol obtained by the first distillation, may be carried out by means of a multidistillation apparatus. For example, FIG. 2 illustrates a case where the second distillation column and the third distillation column are employed. Further, each distillation may be carried out in a continuous system or in a batch system.

FIG. 3 is a flow chart of a case which includes a step of further distilling the fraction (hereinafter referred to as the first fraction) from the first distillation in order to recover methanol from the first fraction. As shown in FIG. 3, the first fraction recovered from the top of the distillation apparatus (the first distillation column in the FIG.) in the first distillation step (the first fraction may contain tert-butyl alcohol, HF and water in addition to methanol), will be led to another distillation apparatus (the second distillation column in FIG. 3). Methanol is recovered as the fraction (hereinafter referred to as the second fraction) obtainable from the top by distillation in the second distillation column. The methanol recovered as the second fraction, is high purity methanol, and accordingly, it can be returned to the reactor and re-used for the reaction with tetrafluoroethylene or hexafluoropropylene. The amount of HF in the methanol as the second fraction is preferably at most 10 ppm.

In the foregoing, a description is made with reference to a case where $C(CH_3)_3-O-O-C(CH_3)_3$ is used as the alkyl peroxide. However, the same will apply also to a case where another alkyl peroxide is used as a radical initiator.

With the fluorinated alcohol of the formula (1) which can be obtained in high purity by the process of the present invention, the evaporation residue will be at most 50 ppm in a usual case. Such a fluorinated alcohol is useful as a solvent for a process for preparing a recording layer of an information recording medium having a recording layer capable of writing and/or reading information by a laser, formed on a substrate.

Namely, the information recording medium having a recording layer capable of writing and/or reading information by a laser, formed on a substrate, can be produced by forming a recording layer containing a dye in accordance with a conventional method such that the dye is dissolved in a solvent containing the fluorinated alcohol, preferably in a fluorine type solvent containing the fluorinated alcohol, and the obtained solution is coated on the substrate, followed by drying.

As such a dye, a cyanine dye, a phthalocyanine dye, a pyrylium dye, a thiopyrylium dye, a squarylium dye, an azulenium dye, an indophenol dye, an indoaniline dye, a triphenyl methane dye, a quinone dye, an aluminum dye, a diimmonium dye or a metal complex salt dye, may, for example, be mentioned. As the substrate, a plastic such as polycarbonate, polymethyl methacrylate, an epoxy resin, amorphous polyolefin, polyester or polyvinyl chloride, glass or ceramics may be mentioned. Further, an undercoating layer may be formed between the recording layer and the substrate for the purpose of improving the flatness, improving the adhesive strength, preventing modification of the recording layer, etc. A protective layer may be formed on the recording layer.

EXAMPLE

Now, the present invention will be described in further detail with reference to Example. In the following, the amount of water was obtained by a Karl Fischer method; the amount of HF was obtained by a fluorine ion electrode analysis method, and the amounts of organic compounds such as methanol, tert-butyl alcohol and the fluorinated alcohol, were analyzed by gas chromatography, and the respective proportions were obtained as area % of the gas chromatogram.

EXAMPLE

Into an autoclave having an internal capacity of 5 m³ as a reactor, methanol (3 m³) and Perbutyl D (20 kg) as an alkyl peroxide, were charged, and the autoclave was flushed with nitrogen and then heated to 125° C., whereupon tetrafluoroethylene was continuously supplied so that the internal pressure would be 0.8 MPa and reacted for 16 hours. The reaction crude liquid after the reaction contained 100 ppm of unreacted Perbutyl D, 8,000 ppm of tert-butyl alcohol, 1,500 ppm of HF, 3,000 ppm of water and methanol as other component. To this reaction crude liquid, water was added so that the content of water would be 5 mass %. This was led to the first distillation column in accordance with the flow chart shown in FIG. 1, and while controlling the pressure to a level of 0.1 MPa, the still was heated, and the reaction crude liquid was separated into a column top fraction containing methanol, tert-butyl alcohol, HF and water, distilled from the top of the distillation column at the distillation temperature of from 65 to 100° C., and a bottom liquid containing the fluorinated alcohol recovered from the bottom section. Tert-butyl alcohol in the bottom liquid was reduced to a level of not more than 100 ppm. The bottom liquid was charged into a distillation apparatus having a theoretical plate number of 40 plates, and purification was carried out by batch distillation (distillation conditions: 0.025 MPa, 65 to 80° C.), whereby $HCF_2CF_2CH_2OH$ was obtained at a recovery of 80% based on $HCF_2CF_2CH_2OH$ in the reaction crude liquid. The purity of the obtained $HCF_2CF_2CH_2OH$ was at least 99.9 mass %, and the evaporation residue was not more than 50 ppm.

On the other hand, the fraction recovered from the top of the first distillation column contained 150 ppm of Perbutyl D, 15,000 ppm of tert-butyl alcohol, 2,800 ppm of HF, 8 mass % of water and methanol. This fraction was introduced into another distillation column (corresponding to the second distillation column in FIG. 3) and distilled (distillation conditions: 0.1 MPa, 65° C.), whereby methanol containing not more than 10 ppm of tert-butyl alcohol, not more than 10 ppm of HF and not more than 1,000 ppm of water, was recovered from the top of the second distillation column.

INDUSTRIAL APPLICABILITY

According to the present invention, a high purity fluorinated alcohol such as $HCF_2CF_2CH_2OH$, $H(CF_2CF_2)_2CH_2OH$ or $HCF(CF_3)CF_2CH_2OH$, which is useful for the production of a photoreceptor of a film, or an information recording medium (such as an optical disk such as CD-R or DVD-R) having a recording layer capable of writing and/or reading information by a laser, formed on a substrate, can be obtained in a high purification yield by purification in a small number of steps. Further, methanol used in an excess amount, can be recovered after the reaction and re-used. Further, in a case where the fluorinated alcohol obtained by the present invention, is obtained as a distillate component, there is a merit such that there will be no inclusion of a distillation residue.

The entire disclosure of Japanese Patent Application No. 2000-254433 filed on Aug. 24, 2000 including specification, claims, drawings and summary is incorporated herein by reference in its entirety.

What is claimed is:

1. A process for producing a fluorinated alcohol, which comprises:

reacting methanol with tetrafluoroethylene or hexafluoropropylene in the presence of an alkyl peroxide to produce a fluorinated alcohol of the following formula (1) in a reaction liquid:

$H(CFR^1CF_2)_nCH_2OH$ (1)

wherein n is 1 or 2, and when n is 1, $R^1$ is F or $CF_3$, and when n is 2, $R^1$ is F, distilling the reaction liquid after completion of the reaction in the presence of water and HF to separate into a fraction containing an alcohol derived from the alkyl peroxide and a bottom liquid containing the fluorinated alcohol of the formula (1), and then, purifying the bottom liquid to recover the fluorinated alcohol of the formula (1);

wherein an evaporation residue of the fluorinated alcohol is at most 50 ppm.

2. The process for producing a fluorinated alcohol according to claim 1, wherein the fraction comprises methanol, water and HF.

3. The process for producing a fluorinated alcohol according to claim 2, wherein the fraction is further distilled, and the distilled methanol is reused for the reaction.

4. The process for producing a fluorinated alcohol according to claim 1, wherein the distillation of the reaction liquid is carried out using a distillation column, and the fraction is distilled from the top of the distillation column.

5. The process for producing a fluorinated alcohol according to claim 1, wherein the bottom liquid after the distillation contains the alcohol derived from the alkyl peroxide in an amount of not more than 1000 ppm, not including 0.

6. The process for producing a fluorinated alcohol according to claim 1, wherein the distillation is carried out with the reaction liquid adjusted to contain from 0.01 to 10 mass % of HF and from 0.1 to 10 mass % of water.

7. The process for producing a fluorinated alcohol according to claim 1, wherein the distillation conditions are such that the gauge pressure during the distillation is from 0 to 0.1 MPa, and the distillation temperature is from 40 to 130° C.

8. The process for producing a fluorinated alcohol according to claim 1, wherein the alkyl peroxide is a compound of the following formula (2a), and the reaction is carried out at a temperature of form 100° C. to 140° C.:

$C(CH_3)_3$—O—O—$R^2$ (2a) wherein $R^2$ is a $C_{1-20}$ aliphatic hydrocarbon group or an aromatic hydrocarbon group.

9. The process for producing a fluorinated alcohol according to claim 1, wherein the purification of the bottom liquid is carried out by distillation using a distillation column, and the fluorinated alcohol of the formula (1) is distilled from the top of the column.

10. The process for producing a fluorinated alcohol according to claim 1, wherein the distillation is carried out with the reaction liquid adjusted to contain from 0.01 to 10 mass % of HF.

11. The process for producing a fluorinated alcohol according to claim 1, wherein the distillation is carried out with the reaction liquid adjusted to contain from 0.1 to 10 mass % of water.

12. The process for producing a fluorinated alcohol according to claim 3, wherein the amount of HF in the distilled methanol obtained by the further distillation of the fraction is at most 10 ppm.

13. The process for producing a fluorinated alcohol according to claim 1, wherein an amount of the alkyl peroxide is from 0.1 to 5 mass % based on the amount of methanol.

14. The process for producing a fluorinated alcohol according to claim 1, wherein an acid acceptor is present during said reaction.

15. The process for producing a fluorinated alcohol according to claim 1, wherein no an acid acceptor is present during said reaction.

16. The process for producing a fluorinated alcohol according to claim 8, wherein said compound of formula (2a) has a half life of from about 8 to 10 hours in the temperature range of from 100 to 140° C.

17. The process for producing a fluorinated alcohol according to claim 1, wherein HF and water are coexistent in sufficient amounts in the reaction liquid before the distillation.

18. The process for producing a fluorinated alcohol according to claim 1, wherein the fraction comprises said alcohol derived from the alkyl peroxide, methanol, water and HF; and wherein the distillation of the reaction liquid is carried out using a distillation column, and the fraction is distilled from the top of the distillation column.

* * * * *